United States Patent [19]

Kangas

[11] 4,303,642
[45] Dec. 1, 1981

[54] STABLE INSECTICIDE CONTAINING LATEXES, METHOD OF MAKING AND METHOD OF DISTRIBUTING INSECTICIDE

[75] Inventor: Donald A. Kangas, Midland, Mich.

[73] Assignee: The Dow Chemical Company, Midland, Mich.

[21] Appl. No.: 147,686

[22] Filed: May 7, 1980

[51] Int. Cl.$^3$ .................... A61K 31/74; A61K 31/78; A01N 57/00
[52] U.S. Cl. ........................................ 424/78; 424/81; 424/200
[58] Field of Search ............................ 424/200, 78, 81

[56] References Cited
U.S. PATENT DOCUMENTS 3,228,830  1/1966  McFadden et al. .
3,400,093  9/1968  Feinberg .
4,071,617  1/1978  Graves et al. .......................... 424/78
4,166,111  9/1979  Cardarelli .............................. 424/78

OTHER PUBLICATIONS

Miller et al. -Chem. Abst. vol. 79 (1973), p. 101,676m.

Primary Examiner—Sam Rosen
Attorney, Agent, or Firm—Merlin B. Davey

[57] ABSTRACT

Stable latexes comprising polymers containing chlorpyrifos or chlorpyrifos-methyl insecticide are prepared by mixing the latex with the insecticide at temperatures of 40° to less than 100° C., with stirring. The polymer granules protect the dissolved insecticide from early leaching or decomposition and prolong the effect and soil penetration of the toxicant.

10 Claims, No Drawings

STABLE INSECTICIDE CONTAINING LATEXES, METHOD OF MAKING AND METHOD OF DISTRIBUTING INSECTICIDE

BACKGROUND OF THE INVENTION

1. Field of the Invention

This invention relates to novel compositions comprising certain polymer latexes containing chlorpyrifos or chlorpyrifos-methyl insecticide.

2. Description of the Prior Art

As shown in U.S. Pat. No. 3,400,093 issued Sept. 3, 1968 to Irving Feinberg, known methods for incorporating insecticides into water-based systems have been unsatisfactory in that the insecticide tends to settle out and does not remain uniformly dispersed. Feinberg proposes to solve that problem by emulsion polymerization of monomers in the presence of the insecticide.

However, certain insecticides, such as chlorpyrifos and chlorpyrifos-methyl, tend to hydrolyze if heated to polymerization temperatures for extended periods of time and, in addition, the presence of insecticide in the monomer will influence the polymerization to some degree, e.g., the rate of polymerization, the conversion and/or the molecular weight of the polymer. By adding the insecticide to a finished latex one has an open choice of latex properties and has only to be concerned with the stability of the resulting product.

SUMMARY OF THE INVENTION

This invention provides a stable polymer latex comprising chlorpyrifos or chlorpyrifos-methyl dissolved in the polymeric solids of the latex, said polymeric solids comprising polymers and copolymers of styrene, alkyl styrenes, isoprene, butadiene, acrylonitrile, lower alkyl acrylates, vinyl chloride, vinylidene chloride and $\alpha,\beta$-ethylenically unsaturated carboxylic acids, including polymers containing three or more different monomer species copolymerized therein, the sizes of the polymeric particles being in the range of from 0.03 to 20 microns, preferably 0.1 to 10 microns and most preferably 0.1 to 1 micron. Small amounts, e.g. about 0.5 weight percent or less, of bifunctional vinyl monomers may be employed to cross link the polymers if desired. The preferred polymers and copolymers contain, as a substantial component, i.e. 35 weight percent or more, styrene or an alkylstyrene.

The invention also provides a method of making a stable aqueous insecticide dispersion which comprises adding chlorpyrifos or chlorpyrifos-methyl to a polymer latex wherein the polymer solids comprise polymers and copolymers of styrene, alkyl styrenes, isoprene, butadiene, acrylonitrile, lower alkyl acrylates, vinyl chloride, vinylidene chloride and $\alpha,\beta$-ethylenically unsaturated carboxylic acid, including polymers containing three or more different monomer species copolymerized therein, the sizes of the polymeric particles being in the range of from 0.03 to 20 microns, with stirring at a temperature of 40° to less than 100° C.

DETAILED DESCRIPTION OF THE INVENTION

This invention provides a concentrated aqueous dispersion of insecticide. The insecticide is held in aqueous dispersion by being dissolved in a polymer particle. The polymer particle, by virtue of its composition, stabilizes the insecticide from hydrolysis in the concentrated dispersion and extends its persistence in soil by protecting the active ingredient, once applied to the soil, from degradation due to hydrolysis, soil microbes or ultraviolet light as well as hindering volatilization and, by virtue of its size and surface characteristics stabilizes the concentrated dispersion from coagulation or agglomeration, increases penetration of the insecticide into soil and can increase the efficiency of contact with target organisms.

The aqueous dispersion of insecticide dissolved in small size polymer particles is useful for control of a wide variety of pests and is particularly advantageously employed in the control of sod web worms and grubs in the root zone below the thatch of lawns because the insecticide penetrates through the thatch into the root zone. The dispersion is also useful for maintaining control of organisms for an entire growing season, such as root worm control agents in corn which are applied at seed time but must control root worm larvae through July.

The components of the aqueous insecticide dispersion are insecticide, polymer particles, water and optional adjuvants, such as anionic and nonionic surfactants and dispersants, freezing point depressants, flow aids to prevent caking or aid in the redispersion of bottom sediment, thickening agents and defoamers which may be added to improve the overall properties under field storage and use conditions. The range of proportions for some of these components is as follows:

TABLE I

| Component | Weight % |
| --- | --- |
| Water | 30–50 |
| Insecticide | 10–50 |
| Polymer | 20–40 |
| Anionic Surfactant | 0–5 |
| Nonionic Surfactant | 0–10 |

Insecticides that have been used are chlorpyrifos and chlorpyrifos-methyl. The essential properties of the pesticide are that it is essentially water-insoluble and either liquid or a low melting solid so that it can be solubilized into the polymer at temperatures less than 100° C. as a liquid.

Preparation of Chlorpyrifos in Polystyrene Aqueous Dispersion

The following ingredients were mixed in an Erlenmeyer flask with a magnetic stirrer on a hot plate:

| | |
| --- | --- |
| 65.46 g | Latex of a copolymer of 97 weight percent styrene and 3 weight percent acrylic acid, 0.45 μm particle diameter 46.9 percent solids |
| 30.29 g | Deionized water |
| 3.00 g | Morwet DB (alkyl aryl sulfonate surfactant). |

This mixture was stirred and warmed to 50° C. and then 72.19 g DURSBAN® F (assay 96 percent chlorpyrifos) was added.

The temperature was maintained at about 60° C. and stirring continued for two hours. After cooling to room temperature, no solid material was separated on a filter pad of glass wool. The dispersion was fluid and had a chlorpyrifos content of 40.9 percent and a density of 1.176 g/ml at 25° C. The solid, dried out, formed a clean continuous film, indicating that chlorpyrifos was completely dissolved in polymer particles to form a homogeneous solution.

Aqueous polymer dispersions that have been used to solubilize chlorpyrifos are listed in Table II with the particle size and the maximum amount of chlorpyrifos dissolved in the particle at room temperature.

TABLE II

| | Polymer Composition | Particle Dia, μm | Weight % Chlorpyrifos in Polymer |
|---|---|---|---|
| (1) | Copoly(97 Styrene/-3 Acrylic Acid) | 0.32 | 66.0 |
| (2) | Copoly(97 Styrene/-3 Acrylic Acid) | 0.16 | 40.0 |
| (3) | Copoly(99 Styrene/-1 Itaconic Acid) | 0.14 | 40.0 |
| (4) | Copoly(50 Butyl Acrylate/-47 Styrene/3 Acrylic Acid) | 0.16 | 43.0 |
| (5) | Poly(t-butylstyrene) | 0.17 | 40.0 |
| (6) | Poly(vinyltoluene) | 0.17 | 35.0 |

The amount of chlorpyrifos dissolved in the aqueous dispersion of small size polymer particles is dependent on particle size and interfacial tension between water and polymer as well as the solubility of chlorpyrifos in the polymer. The addition of surfactant increases the amount of chlorpyrifos dissolved in the polymer particles as shown in the following table. The maximum amount of chlorpyrifos dissolved in aqueous dispersion of polymer particles with added DOWFAX® 2A1 surfactant (an alkyl phenoxybenzene disulfonic acid salt having the formula $C_{12}H_{25}C_{12}H_7O(SO_3Na)_2$) is listed in Table III.

TABLE III

| | Polymer Composition | Particle Dia, μm | Weight % Chlorpyrifos in Polymer with DOWFAX® 2A1 Added |
|---|---|---|---|
| (1) | Copoly(97 Styrene/-3 Acrylic Avid) | 0.32 | 71.5 |
| (2) | Copoly(97 Styrene/-1 Itaconic Avid) | 0.14 | 67.6 |
| (3) | Polystyrene | 0.28 | 72.1 |
| (4) | Copoly(54 Styrene/-36 Butadiene) | 0.34 | 72.2 |
| (5) | Copoly(50 Butyl Acrylate/-47 Styrene/3 Acrylic Acid) | 0.16 | 69.4 |
| (6) | Copoly(85 Vinylidene Chloride/15 Methyl Acrylate) | 0.20 | 69.0 |

Aqueous polymer dispersions other than those listed above can be used provided that the insecticide is soluble in the polymer. These aqueous polymer dispersions can be produced by emulsion polymerization or emulsification of polymer solutions or melts in the size range of 0.03 to 20 μm in particle diameter.

Adjuvants may be needed to maintain the stability of the aqueous dispersion of insecticide dissolved in polymer under field operating conditions such as pumping, mixing with other solutions or dispersions and freezing. Some materials which might be used are anionic surfactants such as alkylnapthalene sulfonic acid salts (e.g. Morwet DB-Petrochemicals, Inc.) and DOWFAX® 2A1 surfactant; nonionic surfactants such as ethoxylated alkyl phenols and polyglycols and water-soluble organic materials such as alcohols or glycols.

The increase in soil penetration of insecticide dissolved in small size polymer particle compared to insecticide applied from solvent is shown in Table IV for chlorpyrifos dissolved in 0.32 μm copoly(97 styrene-3-acrylic acid) particles. The test was run by placing the equivalent of 1 lb active insecticide/acre, as a banded treatment, on the surface of 600 g of moist Davis (No. 106) soil in a 1-in diameter tube, 27 in long. After standing overnight, 120 ml of water were added and allowed to run through the soil. After five days the column was sectioned into 1-in increments. Each increment of soil was infested with 50 eggs and 5 last instar larvae of Western spotted cucumber beetle larvae.

TABLE IV

Leaching of Chlorpyrifos in Soil

| Formulation of Chlorpyrifos | Depth in Inches of 100% Larval Control |
|---|---|
| Solvent | 1 |
| 20% in 0.32 μm Copoly (97 styrene-3 acrylic acid) | 5 |
| 37% in 0.32 μm Copoly (97 styrene-3 acrylic acid) | 4 |

The depth, in inches, that no live larvae were found after 48 hours and 10 days is recorded in Table IV as 100 percent larval control.

An increase in efficiency of a soil insecticide dissolved in small size polymer particles compared to insecticide applied from emulsifiable concentrate is demonstrated for certain cases by the data listed in Table V for chlorpyrifos dissolved in the indicated size polymer particles.

TABLE V

Toxicity of Chlorpyrifos to Western Spotted Cucumber Beetle Larvae in Davis (No. 106) Soil

| Formulation of Chlorpyrifos | Chlorpyrifos Concentration ppm in Soil $LC_{50}$ |
|---|---|
| Emulsifiable concentrate | 0.17 |
| 20% in 0.32 μm Copoly(97 styrene-3-acrylic-acid) | 0.3 |
| 37% in 0.32 μm Copoly(97 styrene-3-acrylic acid) | 0.14 |
| 49% in 0.32 μm Copoly(99 styrene-1-itaconic acid) | 0.05 |
| 20% in 0.14 μm Copoly(99 styrene-1-itaconic acid) | 0.07 |
| 39% in 0.14 μm Copoly(99 styrene-1-itaconic acid) | 0.04 |
| 52% in 0.14 μm Copoly(99 styrene-1-itaconic acid) | 0.02 |
| 40% in 6.0 μPolystyrene | 0.6 |

The $LC_{50}$ values listed in Table V were determined from dead larvae count 48 hours after infesting samples of moist Davis (No. 106) soil containing six different concentrations of chlorpyrifos for each formulation with last instar Western spotted cucumber beetle larvae. This data shows that the efficiency is increased with increasing concentration and decreasing particle size.

An increase in the chemical persistence in soil of insecticide dissolved in small polymer particles is demonstrated in Table VI for chlorpyrifos dissolved in various size polymer particles. The fraction of chlorpyrifos remaining, listed in Table VI, was determined by gas chromatographic analysis of acetone extract from the soil by dividing the milligrams of chlorpyrifos detected in the sample by the milligrams added. Minor variations are due to the imprecision of the experimental measurements.

TABLE VI

PERSISTENCE OF CHLORPYRIFOS IN SOIL
Kawkawlin Loam, 17% Moisture, 25° C., Closed

| Time Days | LORSBAN ® 4E 41% Chlorpyrifos Xylene + Surfactant | 20% Chlorpyrifos in Copoly(97 styrene-3-acrylic acid) 0.32 μm Diameter | 35% Chlorpyrifos in Copoly(97-styrene-3-acrylic acid) 0.32 μm Diameter | 20% Chloropyrifos in Polystyrene 10 82 m Diameter |
|---|---|---|---|---|
| 0 | 1.1 | 1.02 | 1.01 | 0.95 |
| 1 | 1.0 | — | — | — |
| 3 | 1.0 | 1.00 | 0.92 | — |
| 7 | 0.69 | 0.87 | 0.87 | 1.16 |
| 14 | 0.47 | 0.79 | 0.63 | 0.89 |
| 21 | 0.40 | 0.75 | 0.56 | 0.79 |
| 28 | 0.36 | 0.83 | 0.58 | 0.89 |
| 29 | 0.36 | 0.71 | 0.51 | — |
| 42 | 0.26 | 0.66 | 0.44 | 0.79 |
| 51 | 0.25 | 0.66 | 0.47 | — |
| 63 | — | 0.61 | 0.40 | 0.68 |
| 64 | 0.22 | — | — | — |
| 70 | 0.20 | 0.67 | 0.44 | — |
| 84 | — | 0.62 | 0.38 | 0.56 |

What is claimed is:

1. A stable polymer latex comprising chlorpyrifos or chlorpyrifos-methyl dissolved in the polymeric solids of the latex, said polymeric solids comprising polymers and copolymers of styrene, alkyl styrenes, isoprene, butadiene, acrylonitrile, lower alkyl acrylates, vinyl chloride, vinylidene chloride and α,β-ethylenically unsaturated carboxylic acids, including polymers containing three or more different monomer species copolymerized therein, the sizes of the polymeric particles being in the range of from 0.03 to 20 microns.

2. Latex of claim 1 wherein the polymeric solids comprise styrene or an alkylstyrene as a substantial component.

3. Latex of claim 1 wherein the polymer particles are in the size of from 0.1 to 10 microns.

4. Latex of claim 3 wherein the polymer particles are in the size of from 0.1 to 1.0 microns.

5. Latex of claim 1 comprising 30 to 50 weight percent water, 10 to 50 weight percent chlorpyrifos or chlorpyrifos-methyl, 20 to 40 weight percent polymer solids, 0 to 5 weight percent anionic surfactant and 0 to 10 weight percent nonionic surfactant.

6. Latex of claim 5 wherein the polymer comprises styrene or an alkylstyrene as a substantial component.

7. Method of making a stable aqueous insecticide dispersion which comprises adding chlorpyrifos or chlorpyrifos-methyl to a polymer latex wherein the polymer solids comprise polymers and copolymers of styrene, alkyl styrenes, isoprene, butadiene, acrylonitrile, lower alkyl acrylates, vinyl chloride, vinylidene chloride and α,β-ethylenically unsaturated carboxylic acids, including polymers containing three or more different monomer species copolymerized therein, the sizes of the polymeric particles being in the range of from 0.03 to 20 microns, with stirring at a temperature of 40° to less than 100° C.

8. Method of claim 7 wherein the polymer comprises styrene or an alkylstyrene as a substantial component.

9. Method of distributing chlorpyrifos or chlorpyrifos-methyl for the control of soil dwelling insects which comprises applying the chlorpyrifos or chlorpyrifos-methyl to the soil in the form of an aqueous dispersion of polymer particles containing the chlorpyrifos or chlorpyrifos-methyl dissolved therein.

10. Method of claim 9 wherein the insect is the corn root worm.

* * * * *